US008224011B2

(12) United States Patent
Heringslack

(10) Patent No.: US 8,224,011 B2
(45) Date of Patent: Jul. 17, 2012

(54) EAR CUP WITH MICROPHONE DEVICE

(75) Inventor: Henrik Heringslack, Varnamo (SE)

(73) Assignee: 3M Innovative Properties Company, St. Paul, MN (US)

( * ) Notice: Subject to any disclaimer, the term of this patent is extended or adjusted under 35 U.S.C. 154(b) by 1083 days.

(21) Appl. No.: 11/912,608

(22) PCT Filed: Apr. 26, 2006

(86) PCT No.: PCT/SE2006/000498
§ 371 (c)(1),
(2), (4) Date: Oct. 25, 2007

(87) PCT Pub. No.: WO2006/118516
PCT Pub. Date: Nov. 9, 2006

(65) Prior Publication Data
US 2008/0187150 A1   Aug. 7, 2008

(30) Foreign Application Priority Data
Apr. 29, 2005 (SE) ........................................ 0500983

(51) Int. Cl.
*H04R 9/08* (2006.01)
*H04R 25/00* (2006.01)
*H03B 29/00* (2006.01)

(52) U.S. Cl. ........ 381/355; 381/71.6; 381/71.7; 381/72; 381/369; 381/370; 381/371; 381/375

(58) Field of Classification Search ................. 381/71.6, 381/71.7, 72, 355, 369, 370, 371, 375
See application file for complete search history.

(56) References Cited

U.S. PATENT DOCUMENTS

| 3,087,028 A | 4/1963 | Bonnin |
| 3,306,991 A | 2/1967 | Wood |
| 3,394,226 A | 7/1968 | Andrews, Jr. |
| 3,529,102 A * | 9/1970 | Rosenstand ................... 381/324 |

(Continued)

FOREIGN PATENT DOCUMENTS
DE      0465971 A2    1/1992
(Continued)

OTHER PUBLICATIONS

International Search Report; PCT/SE2006/000498; Aug. 8, 2006.

*Primary Examiner* — Elvin G Enad
*Assistant Examiner* — Tsz Chan
(74) *Attorney, Agent, or Firm* — Emily M. Van Vliet

(57) ABSTRACT

An ear cup with a microphone apparatus including an inner cup portion, for forming a noise damping space, and an outer cup portion for forming a space for accommodating electronics and/or a current source. The inner cup portion and the outer cup portion are separated by a partition. The inner cup portion has a pocket and two opposingly located recesses in which a bracket for a microphone is disposed. Over the microphone, a windshield is provided, this protecting the microphone from being damaged and also damping wind noise. The windshield has an outer configuration that may be seen as a continuation of the outer cup portion, in order to prevent turbulence in the region of the windshield. The windshield is produced from a porous material, which is surrounded by a mounting frame having nap catches for engagement in snap catches.

12 Claims, 5 Drawing Sheets

U.S. PATENT DOCUMENTS

| | | |
|---|---|---|
| 3,869,584 A | 3/1975 | Wilde |
| 3,890,474 A | 6/1975 | Glicksberg |
| 3,947,646 A * | 3/1976 | Saito ............................ 381/368 |
| 3,952,158 A | 4/1976 | Kyle |
| 4,025,734 A | 5/1977 | Alcupis |
| 4,064,362 A | 12/1977 | Williams |
| 4,087,653 A | 5/1978 | Frieder, Jr. |
| 4,088,849 A | 5/1978 | Usami |
| 4,150,262 A | 4/1979 | Ono |
| 4,302,635 A | 11/1981 | Jacobsen |
| 4,455,675 A | 6/1984 | Bose |
| 4,588,868 A | 5/1986 | Bertagna |
| 4,644,581 A | 2/1987 | Sapiejewski |
| 4,833,719 A | 5/1989 | Carme |
| 4,867,149 A | 9/1989 | Falco |
| 4,887,693 A * | 12/1989 | Plice ............................ 181/242 |
| 4,928,311 A | 5/1990 | Trompler |
| 4,985,925 A | 1/1991 | Langberg |
| 5,125,032 A | 6/1992 | Meister |
| 5,182,774 A * | 1/1993 | Bourk ............................ 381/71.6 |
| 5,251,263 A | 10/1993 | Andrea |
| 5,404,577 A | 4/1995 | Zuckerman |
| 5,450,496 A | 9/1995 | Burris |
| 5,550,923 A | 8/1996 | Hotvet |
| 5,631,965 A | 5/1997 | Chang |
| 5,675,658 A | 10/1997 | Brittain |
| 5,701,355 A * | 12/1997 | Brannan et al. ............... 381/361 |
| 5,870,483 A * | 2/1999 | Wong et al. ................... 381/189 |
| 6,412,593 B1 | 7/2002 | Jones |
| 6,463,157 B1 | 10/2002 | May |
| 6,567,525 B1 | 5/2003 | Sapiejewski |
| 6,574,345 B1 * | 6/2003 | Huang ............................ 381/380 |
| 6,597,792 B1 * | 7/2003 | Sapiejewski et al. ........ 381/71.6 |
| 6,631,279 B2 | 10/2003 | Rivera |
| 6,704,428 B1 | 3/2004 | Wurtz |
| 6,748,087 B1 | 6/2004 | Jones |
| 6,801,629 B2 | 10/2004 | Brimhall |
| 6,965,681 B2 | 11/2005 | Almqvist |
| 6,970,571 B2 | 11/2005 | Knorr |
| 7,245,735 B2 | 7/2007 | Han |
| 7,308,106 B2 | 12/2007 | Vaudrey |
| 7,327,850 B2 | 2/2008 | Crump |
| 7,391,878 B2 | 6/2008 | Liao |
| 7,664,282 B2 | 2/2010 | Urso |
| 8,054,985 B2 | 11/2011 | Doty |
| 2001/0046304 A1 | 11/2001 | Rast |
| 2002/0055374 A1 * | 5/2002 | Rivera ............................ 455/569 |
| 2002/0080987 A1 | 6/2002 | Almqvist |
| 2002/0106100 A1 * | 8/2002 | Kao ............................ 381/381 |
| 2004/0125976 A1 | 7/2004 | Reneker |
| 2006/0050914 A1 * | 3/2006 | Urso et al. ................... 381/328 |
| 2007/0274529 A1 | 11/2007 | Nordin |
| 2008/0011084 A1 | 1/2008 | Von Dach |

FOREIGN PATENT DOCUMENTS

| | | |
|---|---|---|
| DE | 10117704 | 9/2001 |
| EP | 0967592 | 12/1999 |
| EP | 1629808 A1 | 3/2006 |
| GB | 1160431 A | 8/1969 |
| GB | 1289993 | 9/1972 |
| GB | 2445984 A | 7/2008 |
| WO | WO 87/04065 | 7/1987 |
| WO | WO 91/07153 | 5/1991 |
| WO | WO 96/08004 | 3/1996 |
| WO | WO 97/28742 A1 | 8/1997 |
| WO | WO 02/17838 | 3/2002 |
| WO | WO 2005/051255 | 6/2005 |
| WO | WO 2006/118514 | 11/2006 |
| WO | WO 2008/099137 | 8/2008 |
| WO | WO 2008/113822 | 9/2008 |

* cited by examiner

EAR CUP WITH MICROPHONE DEVICE

TECHNICAL FIELD OF THE INVENTION

The present invention relates to an ear cup with a microphone apparatus and comprising: a first, inner cup portion for forming a noise damping space, a second, outer cup portion for forming a space for accommodating electronics and/or a current source, a partition separating the two spaces from one another, and a microphone provided with a windshield of porous material for receiving sound from the surroundings.

BRIEF DISCUSSION OF RELATED ART

A large number of hearing protection units are previously known in the art which are equipped for communication. Such hearing protection units have at least one, but in certain cases two microphones for receiving sound from the surroundings. Usually, the microphones are placed on the outside of the ear cups and are surrounded by a body of porous foamed material for damping wind noise.

Unfortunately, such a solution functions poorly, since the wind noise is only partly damped. Furthermore, the exterior positioning of the microphone with the projecting windshield suffers from practical drawbacks in that it may easily be damaged, for example by branches.

BRIEF SUMMARY OF THE INVENTION

The present invention provides an ear cup such that the drawbacks inherent in the prior art technology are obviated or at least substantially reduced. In particular, the present invention provides an ear cup where noise from the wind is damped in a very efficient manner and where the risk of mechanical damage to the windshield or the microphone is reduced to a minimum.

The invention an ear cup where the microphone is disposed on the inside of the outer cup portion, which has an opening in front of the microphone, the outer surface of the windshield is disposed as a continuation of the external surfaces of the outer cup portion, these external surfaces coextending adjacent with the windshield, and a cavity is disposed between the inside of the windshield and the opening.

BRIEF DESCRIPTION OF THE DRAWINGS

The present invention will now be described in greater detail hereinbelow, with reference to the accompanying Drawings. In the accompanying Drawings.

DETAILED DESCRIPTION OF THE INVENTION

In the description given below, use will be made of directional- and positional indications. These refer to a situation where a complete hearing protection unit with two ear cups and a crown stirrup or strap is worn in the normal manner with the crown stirrup or strap extending up over the wearer's head. Thus, for example, the expressions 'outwards' and 'inwards' will be employed in the meaning of facing away from the wearer's head and in towards the wearer's head, respectively.

Figure 1:
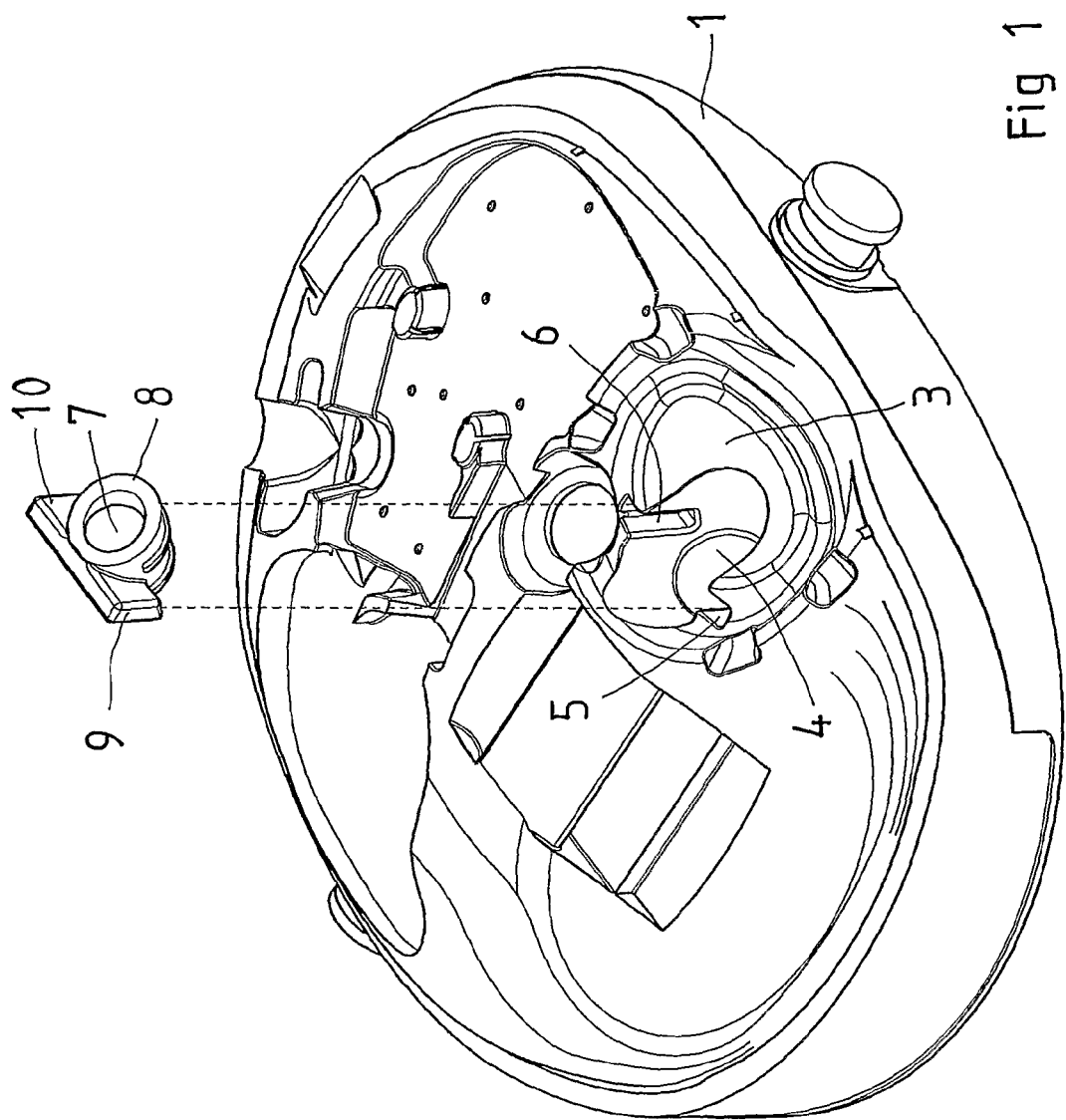
FIG. 1 shows an inner cup portion included in the ear cup, as well as a unit consisting of a microphone and bracket prior to the mounting of the microphone.
Figure 2:
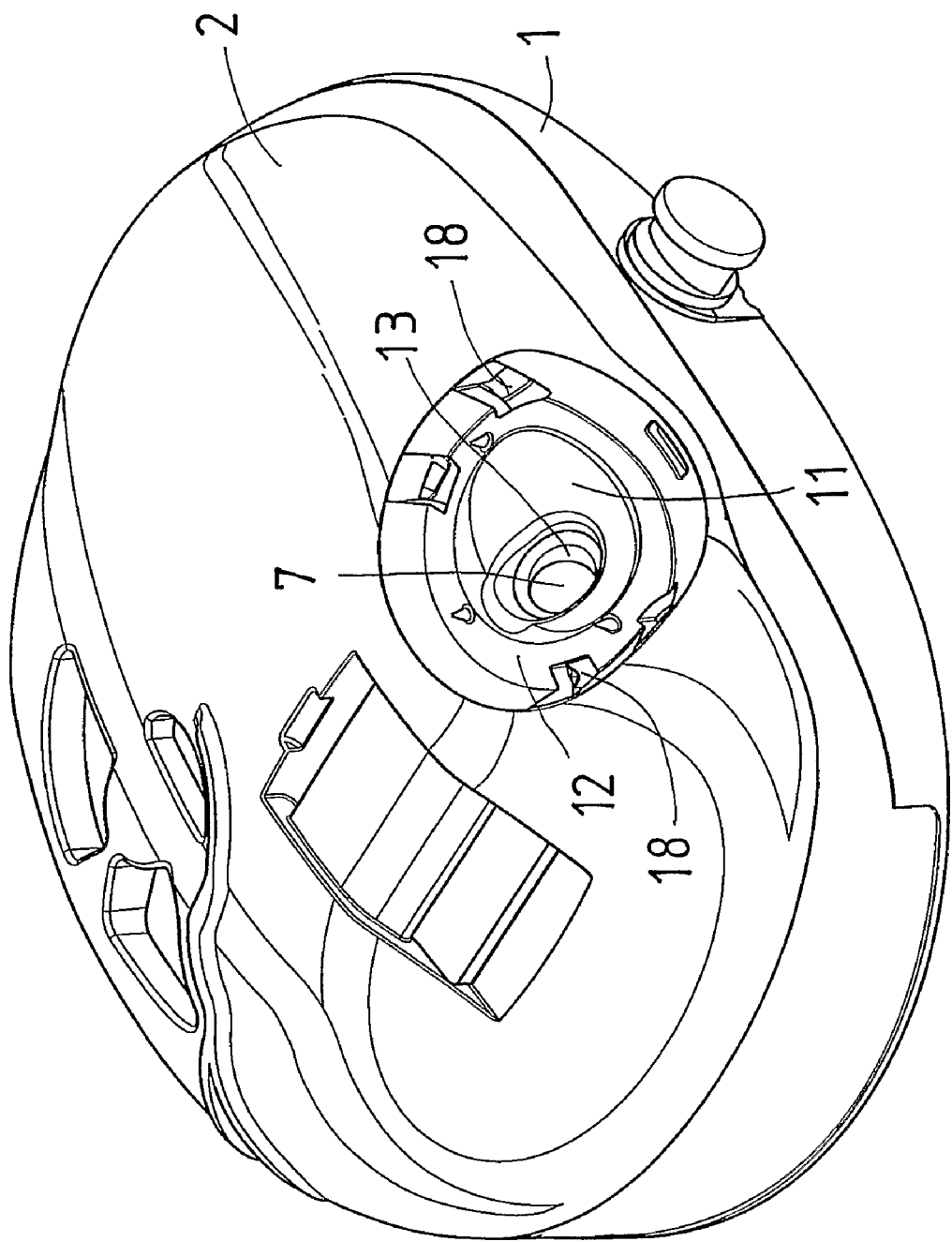
FIG. 2 is a view corresponding to that of FIG. 1 of the ear cup, with an outer cup portion mounted in position.
Figure 3:
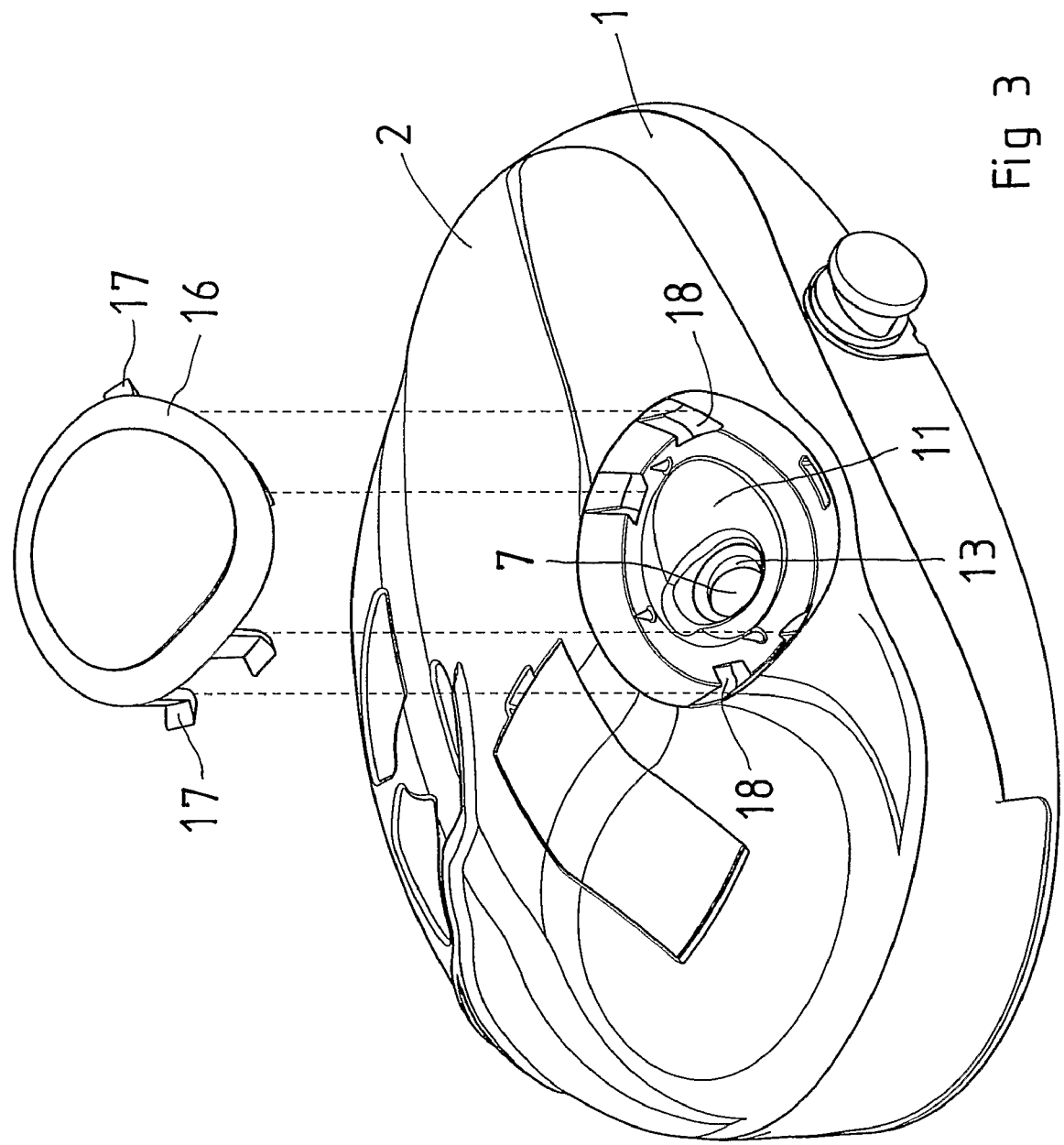
FIG. 3 shows the ear cup according to FIG. 2 prior to the mounting of a windshield, a frame for retaining the windshield being shown prior to the mounting of the frame.

FIGS. 1 to 3 show the right-hand one of the two ear cups included in a complete hearing protection unit. It will be apparent from these Figures that the ear cup comprises a first or inner cup portion 1 and a second or outer cup portion 2. It will be apparent from FIG. 1 that the inner cup portion 1 has, on its outside, an inward bulge 3 which is associated with a pocket 4, which is thus open towards the inward bulge 3. Both the inward bulge 3 and the pocket 4 are closed towards the inside of the inner cup portion. The pocket 4 has two opposingly located recesses 5 and 6.

A microphone 7 is disposed in a bracket 8 which has wings 9 and 10 projecting in opposing directions, the wings lying in a common plane which intersects the longitudinal axis 19 (FIG. 7B) of the bracket at an acute angle. Both of the wings 9 and 10 are formed so as to fit in the recesses 5 and 6, respectively, when the bracket 8 is displaced downwards in the pocket 4. By such means, the microphone will be positionally fixed in the pocket 4 so that its sound receiving surface is turned to face towards the inward bulge 3 and is freely exposed to it. The sound receiving surface of the microphone 7 thus 'looks' along the axis 19. The direction of the pocket 4 is such that the centre axis 19 of the bracket 8, when the ear cup is located in a position of use, will extend obliquely out to the right in a forward direction in relation to the wearer of the hearing protection unit (this applies to the right-hand ear cup). For the left-hand ear cup, the corresponding axis points forwards and obliquely outwards to the left.

While this is not shown in FIG. 1, the microphone 7, the bracket 8 and the connection conductor or lead of the microphone are joined together to form an integrated unit and, from the pocket 4, a conductor receiving space extends to a position on the outside of the inner cup portion 1, where electric connection for the microphone 7 is to be put into effect.

Figure 4:
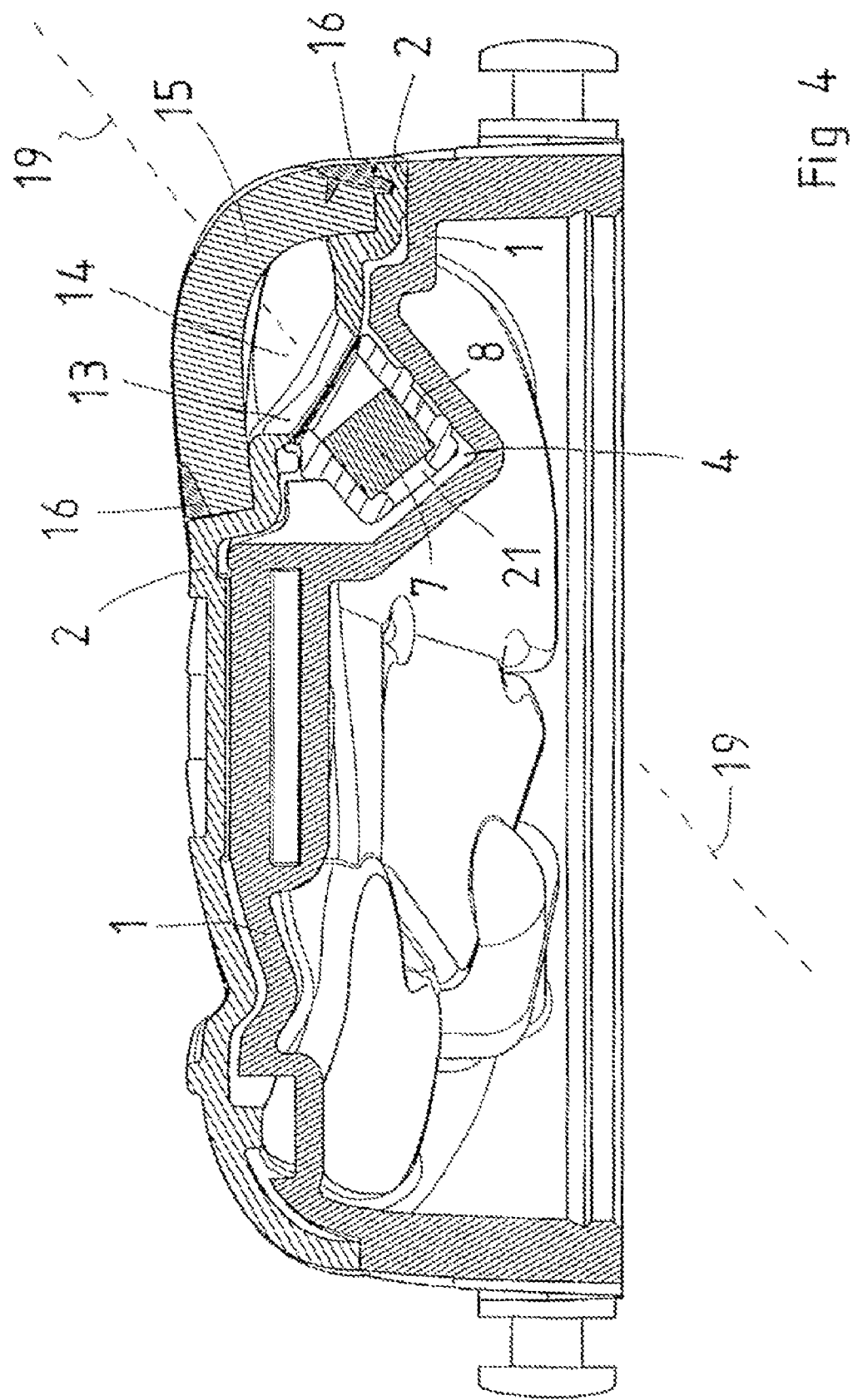
FIG. 4 is a horizontal cross section through a complete ear cup on a level with the microphone.

FIG. 4 shows in cross section how the microphone 7 is disposed interiorly in the bracket 8 and this in turn is positioned in the pocket 4 on the outside of the inner cup portion 1. It will also be apparent from FIG. 4 that the outer cup portion 2 covers the inner cup portion on its outside.

In FIG. 2, the outer cup portion 2 has been mounted on the inner cup portion 1 and it will be apparent that the outer cup portion 2 completely covers the whole of the outside of the inner cup portion 1 and that the outer cup portion 2 has, on its outside, an inward bulge 11, which is surrounded by a countersunk flange 12 which is open towards the outer surface of the outer cup portion 2. (The purpose of this flange will be described in greater detail below). At the inner end of the inward bulge 11, there is an opening 13 which lies in front of and preferably straight in line with the microphone 7. In such instance, the size of the opening is at least as large as the transverse dimension of the microphone 7, but preferably slightly larger, however not so large that the outer diameter of the bracket 8 is reached or surpassed. Thus, otherwise expressed, the microphone 7 'looks to the front' through the opening 13 in the bottom or the inner end of the inward bulge 11. It will further be apparent from FIG. 4 that the distance between the inside of the outer cup portion 2 and the microphone bracket 8 is insignificant. The inward bulge 11 on the inside of the outer cup portion 2 forms an arched funnel-shaped cavity 14 where the microphone 7 is located at the inner end of the cavity or its bottom. The surface on the outside of the outer cup portion 2 defining the cavity 14 may be made hemispherical or at least approximately hemispherical.

The above-mentioned flange 12 around the inward bulge 11 in the outer cup portion 2 is intended for accommodating a windshield 15 (see FIG. 4) which is produced from a porous material, preferably a foamed material with open pores. The cavity 14 is located thus on the inside of the windshield 15 and between this and the microphone 7.

In order to prevent turbulence and in particular turbulence in the region at the windshield 15, this is countersunk in the outer surface of the outer cup portion 2 in such a manner that the outer defining surface of the windshield can be seen as a continuation of those outer surfaces on the outer cup portion 2 which are adjacent the periphery of the windshield. The outer contour of the windshield should thus merge into and constitute a continuation of the contour of the outer surface of the outer cup portion. As a result of this positioning of the windshield 15, the risk is also avoided that, for example, branches could catch in the windshield and damage it or destroy it.

Figure 5:
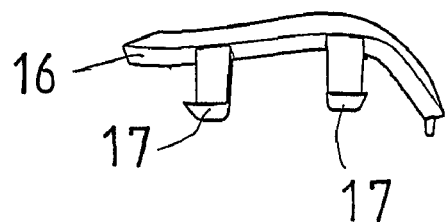
FIG. 5 is a straight side elevation of the frame illustrated in FIG. 3.
Figure 6:
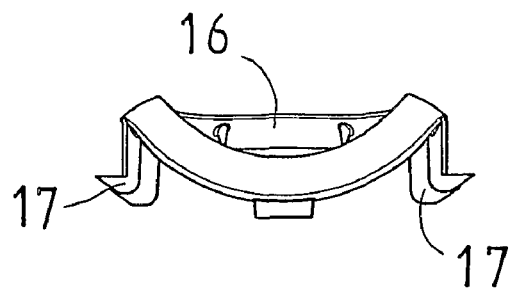
FIG. 6 shows the frame according to FIG. 5 seen from the right in this Figure.

Under reference numeral 16, a mounting frame is shown in FIG. 4, which extends along the periphery of the windshield on its outside and whose purpose is to secure the windshield in the flange 12. Parts of the mounting frame are shown in FIGS. 5 and 6. It is particularly apparent from these Figures that the mounting frame has snap catches 17 which snap into engagement in corresponding catches in the outer cup portion 2. By such means, a soiled or otherwise destroyed windshield 15 may readily be replaceable so that, when necessary, it can be renewed. According to the present invention, it is also possible to mount the windshield using conventional means, i.e. with the aid of a double-sided adhesive tape or an adhesive.

The inward bulge 3 shown in FIG. 1 in the inner cup portion 1 has no acoustic effect on the subject matter of the present invention, but merely serves the purpose of providing room for the inward bulge 11 in the outer cup portion 2.

Figure 7:
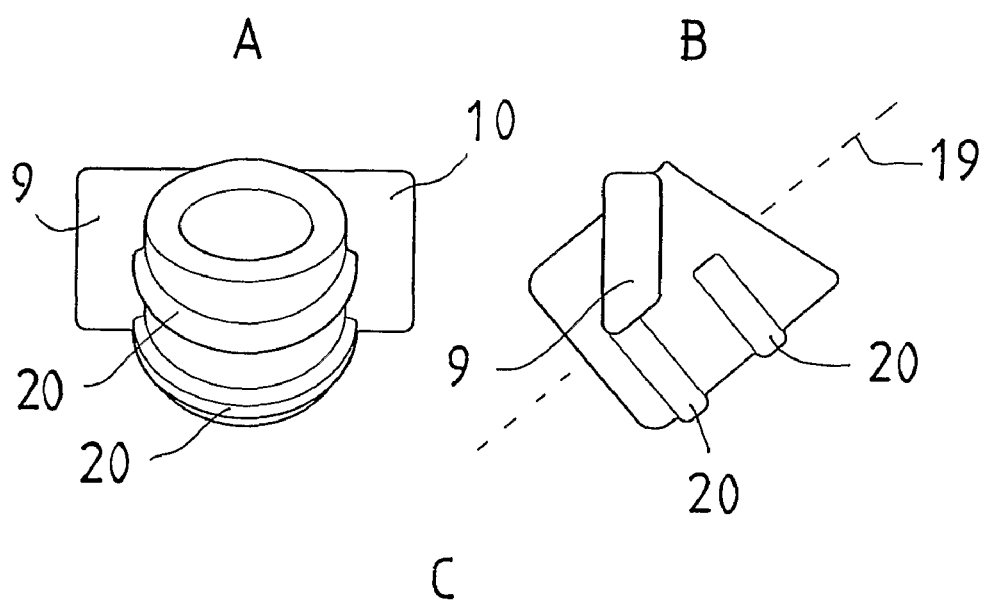
FIG. 7A shows the bracket for the microphone seen straight from the front.
FIG. 7B shows the bracket according to FIG. 7A seen from the side.
FIG. 7C shows the bracket according to FIGS. 7A and 7B seen in the opposite direction compared with FIG. 7A.

FIGS. 7A, 7B and 7C show the microphone bracket 8 and it will be clearly apparent from FIG. 7B how the wings 9 and 10 lie in a plane making an angle with the longitudinal axis 19 of the microphone bracket. The microphone bracket 8 is suitably manufactured from an elastic, yieldable material that may have an inherent noise damping effect but has on its outside grooves 20 which form an acoustic break between the microphone and the wall surfaces defining the pocket 4 in the inner cup portion 1. This entails that the microphone will be less sensitive to such noise as may occur if the ear cup were to come into contact with foreign matter or be subjected to impact or scratching.

It will be apparent from FIG. 4 that the grooves 20 realise an air gap between the outside of the microphone bracket 8 and the above-mentioned defining surfaces in the pocket 4.

As has been mentioned above, the microphone 7, its bracket 8 and the connection conductors of the microphone are integrated into a unit. The connection conductors exit in such instance via an opening 21 in the rear/lower end of the bracket.

What is claimed is:

1. An ear cup with a microphone apparatus comprising:
   a first, inner cup portion for forming a noise damping space,
   a second, outer cup portion for forming a space for accommodating electronics and/or a current source, and
   a microphone provided with a windshield of porous material for receiving sound from the surroundings,
   wherein the microphone is disposed on an outside of the inner cup portion and on an inside of the outer cup portion, which has an opening in front of the microphone, the outer surface of the windshield is disposed as a continuation of external surfaces of the outer cup portion, these external surfaces coextending adjacent with the windshield, and a cavity is disposed between the inside of the windshield and the opening,
   wherein the ear cup is configured to be worn over a user's ear.

2. The ear cup as claimed in claim 1, wherein the cavity is formed
   by an inward bulge in the wall of the outer ear cup portion.

3. The ear cup as claimed in claim 1, wherein the cavity is arched, funnel-shaped with the opening of the microphone at the narrowest portion of the cavity.

4. The ear cup as claimed claim 1, wherein the cavity has a defining surface on an outside of the outer cup portion, this defining surface being approximately hemispherical and having the opening at a deepest part.

5. The ear cup as claimed in claim 1, wherein the microphone is disposed in a pocket on an outside of the inner cup portion, that, in association with the pocket, there is provided a second inward bulge for accommodating the inward bulge in the outer cup portion.

6. The ear cup as claimed in claim 5, wherein the pocket is closed towards the interior of the inner cup portion, and that a conductor accommodating space leads from the pocket to a connection space exteriorly on the inner cup portion.

7. The ear cup as claimed in claim 5, wherein the microphone with its connection conductors is disposed as a unit together with a bracket for positional fixing in the pocket.

8. The ear cup as claimed in claim 7, wherein the bracket has projecting wings for accommodation in corresponding recesses in the pocket.

9. The ear cup as claimed in claim 7, wherein the bracket is produced from a yieldable material for realising an acoustic break between the inner cup portion and the microphone.

10. The ear cup as claimed in claim 1, wherein the windshield is countersunk in a recess or a flange in the outside of the outer cup portion, the recess surrounding the cavity.

11. The ear cup as claimed in claim 1, wherein there is disposed, along the periphery of the windshield and on its outside, a frame whose outer surfaces lie in a plane with adjacent surfaces on the outside of the outer cup portion.

12. The ear cup as claimed in claim 11, wherein the frame and the outer cup portion have mutually cooperating snap connections.

* * * * *

UNITED STATES PATENT AND TRADEMARK OFFICE
CERTIFICATE OF CORRECTION

PATENT NO. : 8,224,011 B2  
APPLICATION NO. : 11/912608  
DATED : July 17, 2012  
INVENTOR(S) : Henrik Heringslack Page 1 of 1

It is certified that error appears in the above-identified patent and that said Letters Patent is hereby corrected as shown below:

Title Page

After "Item [73] Assignee:", insert -- 3M Svenska Aktiebolag, Sollentuna, Sweden --.

Signed and Sealed this  
Fifth Day of February, 2013

Teresa Stanek Rea  
*Acting Director of the United States Patent and Trademark Office*